US010612071B2

(12) United States Patent
Krishnan et al.

(10) Patent No.: US 10,612,071 B2
(45) Date of Patent: Apr. 7, 2020

(54) METHOD OF MEASURING THE DELETERIOUS EFFECTS OF NON-CALORIC ARTIFICIAL SWEETENERS ON ENZYMATIC HYDROLYSIS OF SUCROSE MEASURED IN REAL TIME

(71) Applicant: California State University, Fresno, Fresno, CA (US)

(72) Inventors: Viswanathan Krishnan, Davis, CA (US); Cheenou Her, Fresno, CA (US)

(73) Assignee: California State University, Fresno, Long Beach, CA (US)

( * ) Notice: Subject to any disclaimer, the term of this patent is extended or adjusted under 35 U.S.C. 154(b) by 0 days.

(21) Appl. No.: 15/079,647

(22) Filed: Mar. 24, 2016

(65) Prior Publication Data
US 2019/0264254 A1 Aug. 29, 2019

(51) Int. Cl.
 C12Q 1/40 (2006.01)
 C12Q 1/54 (2006.01)
 G01N 24/08 (2006.01)
 C12Q 1/34 (2006.01)

(52) U.S. Cl.
 CPC ............ *C12Q 1/40* (2013.01); *C12Q 1/34* (2013.01); *C12Q 1/54* (2013.01); *G01N 24/088* (2013.01); *C12Y 302/01026* (2013.01); *G01N 2333/924* (2013.01)

(58) Field of Classification Search
 CPC ... C07H 5/02; C12Q 1/40; C12Q 1/54; G01N 24/088; G01N 2333/924; C12Y 302/01026
 See application file for complete search history.

(56) References Cited

FOREIGN PATENT DOCUMENTS

WO WO 2008096928 A1 * 8/2008 .............. C07H 5/02

OTHER PUBLICATIONS

Omran et al, J. of Toxicol., 2013, vol. 2013 (Article ID: 372986), 6 pages. doi: 10.1155/2013/372986.*
Kehlbeck,JD; Slack,CC; Turnbull,MT; Kohler,SJ "Exploring the Hydrolysis of Sucrose by Invertase Using Nuclear Magnetic Resonance Spectroscopy: A Flexible Package of Kinetic Experiments" J.Chem.Educ., (epub Apr. 3) 2014,91(5),734-738. doi:10.1021/ed300889s.*
Her, C; Alonzo, AP; Vang,JY; Torres,E; Krishnan,VV "Real-Time Enzyme Kinetics by Quantitative NMR Spectroscopy and Determination of the Michaelis-Menten Constant Using the Lambert-W Function" J. Chem Ed. J. Chem. Educ., (epub Aug. 18) 2015, 92, 1943-1948. DOI: 10.1021/acs.jchemed.5b00136.*
Baird I. M., N. W. Shephard, R. J. Merritt and G. Hildick-Smith (2000). "Repeated dose study of sucralose tolerance in human subjects." Food Chem Toxicol 38 Suppl 2: S123-129.

Barry, D. A., J. Y. Parlange, L. Li, H. Prommer, C. J. Cunningham and E. Stagnitti (2000). "Analytical approximations for real values of the Lambert W-function." Mathematics and Computers in Simulation 53(1-2): 95-103.
Bezerra, R. M. F. and A. A. Dias (2007). "Utilization of integrated Michaelis-Menten equation to determine kinetic constants." Biochemistry and Molecular Biology Education 35(2): 145-150.
Bogan, J. S. (2012). "Regulation of glucose transporter translocation in health and diabetes." Annu Rev Biochem 81: 507-532.
Briggs, G. E. and J. B. S. Haldane (1925). "A Note on the Kinetics of Enzyme Action." Biochemical Journal 19(2): 338-339.
Corless, R. M., G. H. Gonnet, D. E. G. Hare, D. J. Jeffrey and D. E. Knuth (1996). "On the Lambert W function." Advances in Computational Mathematics 5(4): 329-359.
De Koning, L., V. S. Malik, E. B. Rimm, W. C. Willett and F. B. Hu (2011). "Sugar-sweetened and artificially sweetened beverage consumption and risk of type 2 diabetes in men." Am J Clin Nutr 93(6): 1321-1327.
Dhingra, R., L. Sullivan, P. F. Jacques, T. J. Wang, C. S. Fox, J. B. Meigs, R. B. D'Agostino, J. M. Gaziano and R. S. Vasan (2007). "Soft drink consumption and risk of developing cardiometabolic risk factors and the metabolic syndrome in middle-aged adults in the community." Circulation 116(5): 480-488.
Duggleby, R. G. (2001). "Quantitative analysis of the time courses of enzyme-catalyzed reactions." Methods 24(2): 168-174.
Fagherazzi, G., A. Vilier, D. Saes Sartorelli, M. Lajous, B. Balkau and F. Clavel-Chapelon (2013). "Consumption of artificially and sugar-sweetened beverages and incident type 2 diabetes in the Etude Epidemiologique aupres des femmes de la Mutuelle Generale de l'Education Nationale-European Prospective Investigation into Cancer and Nutrition cohort." Am J Clin Nutr 97(3): 517-523.
"High-Intensity Sweeteners." Written May 19, 2014. Retrieved Apr. 8, 2016, from http://www.fda.gov/Food/IngredientsPackagingLabeling/FoodAdditivesIngredients/ucm397716.htm.
Fowler, S. P., K. Williams, R. G. Resendez, K. J. Hunt, H. P. Hazuda and M. P. Stern (2008). "Fueling the obesity epidemic? Artificially sweetened beverage use and long-term weight gain." Obesity (Silver Spring) 16(8): 1894-1900.

(Continued)

*Primary Examiner* — Aaron J Kosar
(74) *Attorney, Agent, or Firm* — Schwegman Lundberg & Woessner, P.A.

(57) ABSTRACT

Non-caloric artificial sweeteners (NAS) are used as a substitute for natural sugars by providing the sweet taste. This invention measures the effects of artificial sweeteners on the enzyme kinetics of biological systems. The claimed invention is directed to a method of measuring the effect of an artificial sweetener on enzyme-catalyzed hydrolysis of a sugar comprising establishing a first sugar enzymatic conversion rate, then determining a second sugar enzymatic conversion rate, and lastly comparing the first sugar enzymatic rate and the second sugar enzymatic conversion rate. The sugar enzymatic conversion rates can be measured by either nuclear magnetic resonance spectroscopy or a glucometer. The methodology presented may be applied to the elucidation of kinetic parameters for invertase catalyzed conversion of sucrose to glucose and fructose.

9 Claims, 13 Drawing Sheets

(56) References Cited

OTHER PUBLICATIONS

Franks, F., P. J. Lillford and G. Robinson (1989). "Isomeric equilibria of monosaccharides in solution—influence of solvent and temperature." Journal of the Chemical Society-Faraday Transactions I 85: 2417-2426.

Goudar, C. T., S. K. Harris, M. J. McInerney and J. M. Suflita (2004). "Progress curve analysis for enzyme and microbial kinetic reactions using explicit solutions based on the Lambert W function." Journal of Microbiological Methods 59(3): 317-326.

Goudar, C. T., J. R. Sonnad and R. G. Duggleby (1999). "Parameter estimation using a direct solution of the integrated Michaelis-Menten equation." Biochim Biophys Acta 1429(2): 377-383.

Heinzerling, P., F. Schrader and S. Schanze (2012). "Measurement of Enzyme Kinetics by Use of a Blood Glucometer: Hydrolysis of Sucrose and Lactose." Journal of Chemical Education 89(12): 1582-1586.

Heller, A. and B. Feldman (2008). "Electrochemical Glucose Sensors and Their Applications in Diabetes Management." Chemical Reviews 108(7): 2482-2505.

Her, C., A. P. Alonzo, J. Y. Vang, E. Torres and V. V. Krishnan (2015). "Real-Time Enzyme Kinetics by Quantitative NMR Spectroscopy and Determination of the Michaelis-Menten Constant Using the Lambert-W Function." Journal of Chemical Education 92(11): 1943-1948.

Koshland JR, D. E. (2002). "The Application and Usefulness of the Ratio kcat/KM." Bioorganic Chemistry 30(3): 211-213.

Lineweaver, H. and D. Burk (1934). "The Determination of Enzyme Dissociation Constants." Journal of the American Chemical Society 56(3): 658-666.

Ludwig, D. S., K. E. Peterson and S. L. Gortmaker (2001). "Relation between consumption of sugar-sweetened drinks and childhood obesity: a prospective, observational analysis." Lancet 357(9255): 505-508.

Lutsey, P. L., L. M. Steffen and J. Stevens (2008). "Dietary intake and the development of the metabolic syndrome: the Atherosclerosis Risk in Communities study." Circulation 117(6): 754-761.

Mezitis, N. H., C. A. Maggio, P. Koch, A. Quddoos, D. B. Allison and F. X. Pi-Sunyer (1996). "Glycemic effect of a single high oral dose of the novel sweetener sucralose in patients with diabetes." Diabetes Care 19(9): 1004-1005.

Michaelis, L. and M. L. Menten (1913). "Die kinetik der invertinwirkung." Biochem. z 49(333-369): 352.

Nehrling, J. K., P. Kobe, M. P. McLane, R. E. Olson, S. Kamath and D. L. Horwitz (1985). "Aspartame use by persons with diabetes." Diabetes Care 8(5): 415-417.

Schnell, S. and C. Mendoza (1997). "Closed form solution for time-dependent enzyme kinetics." Journal of Theoretical Biology 187(2): 207-212.

Swithers, S. E. (2013). "Artificial sweeteners produce the counterintuitive effect of inducing metabolic derangements." Trends Endocrinol Metab 24(9): 431-441.

Swithers, S. E., A. A. Martin and T. L. Davidson (2010). "High-intensity sweeteners and energy balance." Physiol Behav 100(1): 55-62.

Young, J. K., J. M. Ellison and R. Marshall (2008). "Performance evaluation of a new blood glucose monitor that requires no coding: the OneTouch Vita System." J Diabetes Sci Technol 2(5): 814-818.

\* cited by examiner

METHOD OF MEASURING THE DELETERIOUS EFFECTS OF NON-CALORIC ARTIFICIAL SWEETENERS ON ENZYMATIC HYDROLYSIS OF SUCROSE MEASURED IN REAL TIME

BACKGROUND

1. Field of the Invention

This invention is directed to measuring the effects of artificial sweeteners on the enzyme kinetics of biological systems.

2. Summary of the Prior Art

A. Breakdown of Sugar Essential to Proper Absorption.

Natural sugar in the human diet is made up mostly of sucrose. Furthermore there is a significant increase in the sugar consumption via carbonated soft drinks and energy drinks sweetened with sources of sucrose (including high fructose corn syrup). Sucrose, a disaccharide is not directly digestible. As a first step towards absorption and metabolism, sucrose is enzymatically cleaved to produce monosaccharides so that it can be processed by the intestine. This is the most important step in the process of calorie intake and the downstream process of glucose metabolism.

The enzymatic conversion of sucrose to glucose and fructose follows the classic Michaelis-Menten mechanism, one of the most important enzymatic reactions from yeast to humans. Enzymes catalyze biochemical reactions, speeding up the conversion from substrate to product molecules, which can pass through the intestinal wall and be absorbed by the body. When enzymatic reactions are altered in the very first step of calorie intake, it is expected that rest of the downstream process involving glucose metabolism will also be affected.

B. Natural Artificial Sweeteners (NAS)

Non-caloric artificial sweeteners (NAS), introduced over a century ago provide the sweet taste to foods without adding any calories and is used as a substitute for natural sugars. Currently, there are six different NAS products for use in the United States that are approved by the US Food and Drug Administration: saccharin, aspartame, acesulfame potassium (Ace-K), sucralose, neotame, and advantame (FDA 2015). NAS are regulated as a food additive, unless its use is generally recognized as safe (GRAS). Currently, GRAS notices are pending for two other NAS, steviol glycosides obtained from the leaves of the stevia plant and Siraitia grosvenorii Swingle fruit (monk fruit).

The broader rationale for the wide-spread use of NAS is due to the argument that they can pass through the gastrointestinal tract without being digested. More importantly, it is generally believed that NAS are healthy substitutes for sugars because they provide sweet taste without calories or glycemic effects. Though studies conducted in human subjects with and without diabetes did not affect clinical measures of glucose metabolism (blood glucose level, C-peptide and HBA1c concentration) (Nehrling, Kobe et al. 1985, Corless, Gonnet et al. 1996, Mezitis, Maggio et al. 1996, Baird, Shephard et al. 2000), several epidemiological studies found that negative health effects towards metabolic syndrome, weight gain and type-2 diabetes (Ludwig, Peterson et al. 2001, Dhingra, Sullivan et al. 2007, Fowler, Williams et al. 2008, Lutsey, Steffen et al. 2008, Swithers, Martin et al. 2010, de Koning, Malik et al. 2011, Fagherazzi, Vilier et al. 2013, Swithers 2013).

C. Health Effects

NAS are not physiologically inert and the manner in which they affect the biological process starts from the first step; how sucrose is converted into glucose and fructose. Therefore there is a critical need of a method that can determine how the rate of conversion of sucrose is affected in the presence of NAS. This step is integral to investigate the potential mechanism of energy and glucose homeostasis as well as on metabolic response to an oral glucose load.

SUMMARY OF THE INVENTION

The claimed invention is directed to a method of measuring the effect of an artificial sweetener on enzyme-catalyzed hydrolysis of a sugar comprising: establishing a first sugar enzymatic conversion rate by measuring the rate the sugar breaks down to reaction products in the presence of an enzyme, then determining a second sugar enzymatic conversion rate by measuring the rate the sugar breaks down to reaction products in the presence of the enzyme and the artificial sweetener, and lastly comparing the first sugar enzymatic rate and the second sugar enzymatic conversion rate.

In one aspect of the invention, either the first sugar enzymatic rate or the second sugar enzymatic rate is established by nuclear magnetic resonance. In another aspect of the invention, both the first sugar enzymatic rate and the second sugar enzymatic rate are established by nuclear magnetic resonance.

In yet another aspect of the invention, either the first sugar enzymatic rate or the second sugar enzymatic rate is established by a glucometer. In another aspect of the invention, both the first sugar enzymatic rate and the second sugar enzymatic rate are established by a glucometer.

In still another aspect of the invention, the comparing step results in a numerical value associated with the artificial sweetener. The claimed method may occur in real time. The enzyme may be invertase.

BRIEF DESCRIPTION OF THE FIGURES

FIG. 12A shows a chart demonstrating that increasing sucralose concentration increases the $K_M$ values. FIG. 12B shows a chart demonstrating that increasing sucralose concentration decreases the $V_{max}$. FIG. 12C shows a chart demonstrating the catalytic efficiency of the enzyme activity in the presence of sucralose.

BRIEF DESCRIPTION OF THE PREFERRED EMBODIMENT

Figure 1:
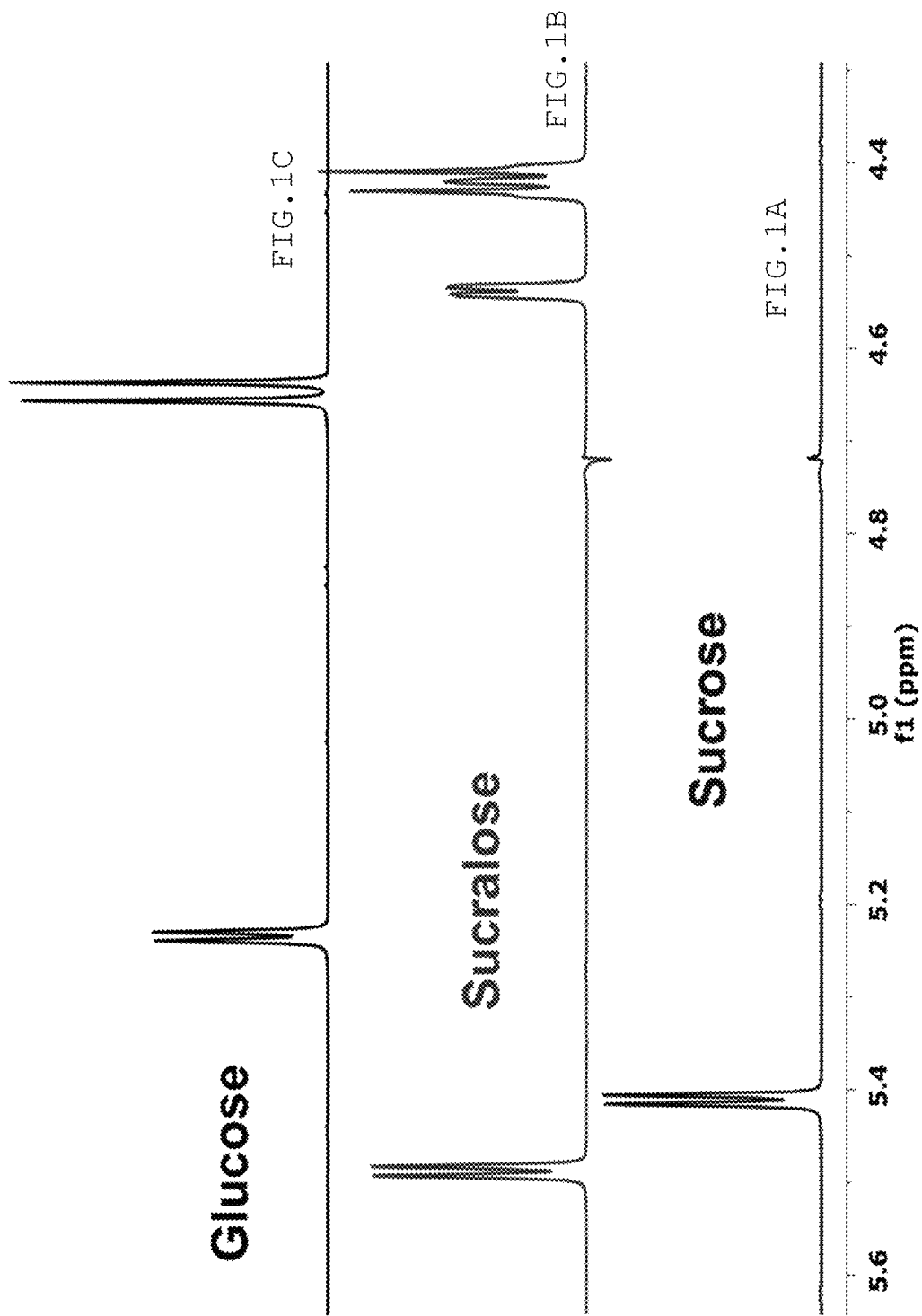
FIG. 1A shows a chart displaying NMR spectra of the substrate sucrose.
FIG. 1B shows a chart displaying NMR spectra of the NAS, sucralose.
FIG. 1C shows a chart displaying NMR spectra of the product glucose.

We invented a novel method to measure the rate of conversion of sucrose to its reaction products in real time, by the enzyme invertase, and to measure the effect a non-caloric artificial sweetener, sucralose, has on the invertase enzymatic reaction of the breakdown of sucrose. This method shows that the enzymatic process of hydrolysis converts the sucrose to glucose, while the concentration of the sucralose is not affected by enzymatic hydrolysis, and therefore remains the same in the presence of invertase. However, the presence of sucralose affects overall kinetics of sucrose hydrolysis.

Breakdown of the sugar in carried out by enzymatic hydrolysis by the enzyme invertase. Scientifically acceptable names for invertase include: alkaline invertase, acid invertase, beta-h-fructosidase, beta-fructosidase, fructosyl-invertase, glucosucrase, invertin, maxinvert L 1000, saccharase, sucrase and the systematic name: beta-fructofuranosidase. Sucrose is hydrolyzed by invertase by cleaving the O-C (fructose) bond and sucrases cleaves the O-C (glucose) bond. Both these enzymatic reactions produce a mixture of glucose and fructose at the end.

Invertase derived from yeast is used for industrial purposes. Bees naturally use the process to make honey from the nectar. Optimum temperature at which the rate of invertase hydrolysis reaction is at its greatest is around 60° C. and an optimum pH of about 4.5.

A. Theoretical Basis for Progress Curve Analysis of Substrate Breakdown.

The catalyzed breakdown or hydrolysis of sucrose can be shown by the Michaelis-Menten equation. The integrated form of the Michaelis-Menten equation using the Lambert-W function was presented by Schnell and Mendoza (Schnell and Mendoza 1997) with application developed by Goudar and co-workers (Goudar, Sonnad et al. 1999, Goudar, Harris et al. 2004). A brief description in relation to enzyme kinetics is given here: The Michaelis-Menten equation in the differential form can be used to describe the dynamics of substrate depletion as Equation [1]:

$$v = \frac{d[P]}{dt} = -\frac{d[S]}{dt} = \frac{V_{max}[S]}{K_M + [S]} \quad [1]$$

As defined in Equation [1], [S] is the substrate concentration, and $V_{max}$ is the maximal rate of enzymatic turnover (sucrose to glucose), and $K_M$ represents the Michaelis-Menten half-saturation constant. The first-order differential equation (Equation [1]) can be integrated to obtain the integral form of the Michaelis-Menten equation (Schnell and Mendoza 1997, Duggleby 2001, Bezerra and Dias 2007) as Equation [2]:

$$K_M \ln\left(\frac{[S]_0}{[S]}\right) + [S]_0 - [S] = V_{max} t \quad [2]$$

The Lambert-W function is a mathematical function and has several applications in computer science, mathematics and physical sciences. (Corless, Gonnet et al. 1996, Barry, Parlange et al. 2000). The Lambert-W function is a form of an exponential function. Mathematically, the exponential function and the natural logarithmic function ln(x) are exponentially related. Similarly W(x) is defined as the inverse of the function satisfying $ye^y = x$ and its solution expressed by the Lambert-W(x) function as y=W(x).

By substituting $y=[S]/K_M$ in Equation [2] and rearranging, we get Equation [3]:

$$ye^y = x(t) \quad [3]$$
$$= \exp\left(\frac{[S]_0 - V_{max}t}{K_M} + \left(\frac{[S]_0}{K_M}\right)\right)$$
$$= \frac{[S]_0}{K_M} \exp\left(\frac{[S]_0 - V_{max}t}{K_M}\right)$$

The left hand side of Equation [3] is analogous to Lambert-W function as shown in the equation in the Corless, Gonnet et al, 1996 article. Thus using the definition of Lambert-W function (y=W(x)), an expression for y could be obtained as that expressed in Equation [4]:

$$y = W\left\{\frac{[S]_0}{K_M} \exp([S]_0 - V_{max}t/K_M)\right\} \quad [4]$$

Further substituting $y=[S]/K_M$ back in Equation [4], we get Equation [5]:

$$[S] = K_M W\left\{\frac{[S]_o}{K_M} \exp\left(\frac{[S]_o - V_{max}t}{K_M}\right)\right\} \quad [5]$$

Equation [5], derived from Equation [2], relates the substrate concentration at any time ([S]) to its initial concentration ([S]$_0$), the Michaelis-Menten kinetic parameters $V_{max}$ and $K_M$. Equation [5] is used to fit the real time experimental data obtained for enzyme kinetics using the analysis code written using R-Statistical environment (R Core Team 2014).

B. Experimental Methods

Invertase (EC 3.2.1.26, β-fructofuranosidase, *S. cerevisiae*) was purchased from Sigma-Aldrich with a specific activity of >300 u/mg of solid (pH 4.6, 303 K). Sucrose, Sucralose, $D_2O$ (99.9 atom % D) and 3-(Trimethylsilyl) propionic-2,2,3,3-$d_4$ acid sodium salt (TSP) were purchased Sigma Aldrich.

A stock acetate buffer solution (26.6 mM acetate (not-deuterated), 15.2 mM acetic acid-$d_4$, 1.2 mM TSP, and pH 4.9) was made. All solutions and dilutions used this stock acetate buffer in order to maintain the same pH 4.9 and the same concentration of TSP (1.2 mM). Using the acetate buffer, a 496 mM stock sucrose solution, 509 mM stock sucralose solution, and a 33 µg/mL stock invertase solution were made. Two standard samples were made in standard 5 mm NMR tubes to set up the NMR parameter. The first standard sample contained only sucrose (40 mM); this standard was used to set up the parameter for the standard (no sucralose) NMR kinetics experiment. The second standard sample contained sucrose (40 mM) and sucralose (40 mM); this standard was used to set up the parameter for the NMR kinetics experiment involving sucralose.

For all the NMR kinetics experiments, the sucrose and invertase concentrations were kept constant at 40 mM and 5 µg/mL, respectively while the sucralose concentrations were varied. The sucralose concentrations used were 1 mM, 5 mM, 10 mM, 20 mM, 40 mM, 60 mM, and 80 mM. All NMR kinetics solutions were made in an Eppendorf tube with a volume of 550 µL prior to adding 100 µL of invertase into the Eppendorf tube then transferring 600 µL of the solution into a NMR tube. The 100 µL invertase solution was added into the Eppendorf tube when the NMR kinetics experiment was ready to start. A timer was set at the beginning of the addition of the invertase solution in order to account for the delay time (the time before the collection of the NMR spectra) as this is a crucial part of the latter calculation.

For all the glucometer kinetics experiments, the invertase concentration (5 µg/mL) and sucrose concentration range (20 mM, 45 mM, 63 mM, 90 mM, 135 mM, 180 mM, and 270 mM) were kept constant at the final volume of 1 mL. There were eight total sets of experiment; one set was with no sucralose (standard run) and the other seven sets (inhibition runs) with the sucralose concentration of 1 mM, 5 mM, 10 mM, 20 mM, 40 mM, 60 mM, and 80 mM. For each set of experiment involving one of the concentration of sucralose, the sucrose concentration was kept constant. All glucometer kinetics solutions were made in an Eppendorf tube with a volume of 900 µL prior to adding 100 µL of invertase. The 100 µL invertase solution was added into the Eppendorf tube when the kinetics experiment was ready to start. A timer was set at the beginning of the addition of the 100 µL invertase solution to the Eppendorf tubes. The glucose concentration of each Eppendorf tube was measured after the reaction was allowed to run for at least 30 minutes.

Enzyme kinetics were performed using ONETOUCH®VitaJ from LifeScan (Young, Ellison et al. 2008). This system is distributed worldwide and normally used at American hospitals. The meters have a measurement range of 20 mg/dL-600 mg/dL glucose. The meters and sensors are available at online pharmacies and the expenses are very low. The general procedure by Heinzerling et al. (Heinzerling, Schrader et al. 2012) was followed except with a minor change of the invertase concentration. The final invertase concentration was 5 µg/mL. A stock acetate buffer solution (66.1 mM acetate, 38.0 mM acetic acid, and pH 5.0) was made. All solutions and dilutions used this stock acetate buffer in order to maintain the same pH 5.0. Using the acetate buffer, a 600 mM stock sucrose solution, 300 mM stock sucralose solution, and a 50 µg/mL stock invertase solution were made. The measurement of the glucose concentration in mg/dL was converted to molarity (M). Data were fit using R-statistical software (R Core Team 2014).

$^1$H-NMR time-course data were collected in real time by qNMR (Vairan-Agilent, VNMRS system) and the kinetic data were subsequently processed using a non-linear least square fit procedure by using the Lambert-W function. This method was applied to determine the effect on the enzyme kinetics of hydrolysis, a fundamental step in converting the sucrose to glucose and fructose. Experimental results obtained using the direct real-time measurements were validated using a glucometer based approach.

C. NMR Spectra of Sucrose Substrate Breakdown

The enzymatic process of hydrolysis converts sucrose to glucose, while the concentration of sucralose is not affected by enzymatic hydrolysis, and therefore remains the same in the presence of invertase. However, as shown in other figures, the presence of sucralose affects overall kinetics of sucrose hydrolysis.

NMR spectra can differentiate between sucrose, glucose and sucralose. FIG. 1A-FIG. 1C show how the NMR spectra of sucrose (FIG. 1A), sucralose (FIG. 1B) and glucose (FIG. 1C) can be differentiated. As shown in FIG. 1A, the NMR spectra for sucrose show a large double peak (doublet) close to the resonance frequency of 5.4 ppm and a small peak at about the resonance frequency of 4.7 ppm (residual water). As shown in FIG. 1B, the NMR spectra for sucralose show a large double peak close to the resonance frequency of 5.5 ppm, a smaller double peak at about the resonance frequency of 4.6 ppm, and a triple peak at a resonance frequency of between 4.4 ppm and 4.5 ppm. As shown in FIG. 1C, the NMR spectra for glucose show a double peak at a resonance frequency between about 5.2 ppm and 5.3 ppm, and two large distinct peaks (doublet), one large peak at about a resonance frequency of about 4.7 ppm and the other large peak at a resonance frequency of slightly below 4.7. The peak at 4.7 ppm belongs to residual water in the sample. Thus the distinct and well resolved respective peaks of sucrose, sucralose and glucose enable a highly sensitive method to differentiate the molecules from one another in the same sample and allow the determination of kinetic rates of conversion due to enzyme action.

Figure 2:
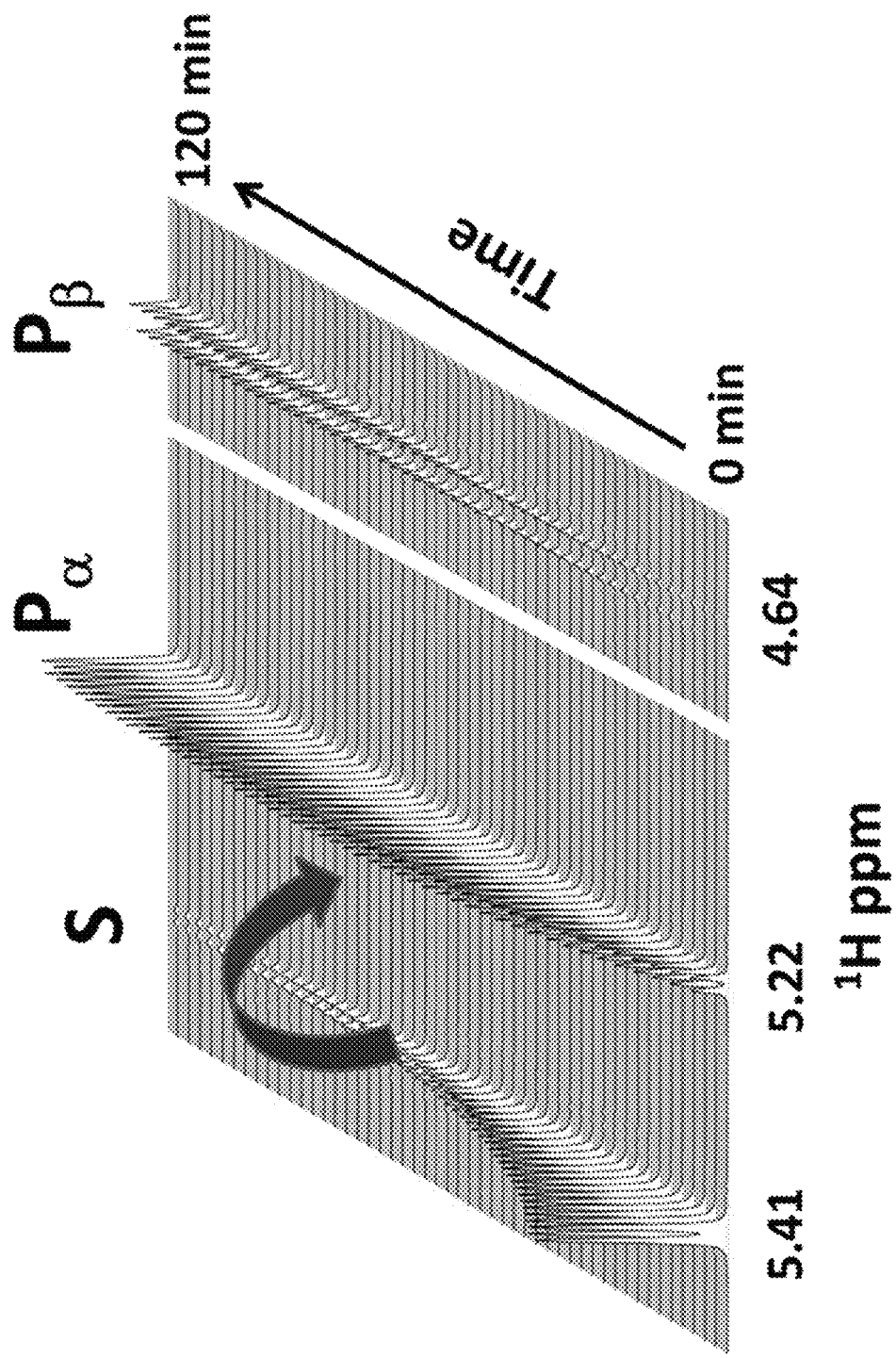
FIG. 2 shows a chart displaying real time measurement of spectral changes of the substrate sucrose broken down into its products.

FIG. 2 shows the real time enzyme kinetics of the substrate ([S], sucrose) converted to the first glucose product ([P]α, glucose) by invertase via hydrolysis. The sucrose resonance (5.41 ppm) completely converted into that of the glucose molecules by the end of the experiment (~120 minutes). As the product a D-glucose at 5.22 ppm forms, it immediately starts to convert into $[P]_β$, representing D-glucose at 4.64 ppm. Glucose exists as a mixture of α- and β-anomers in nature and the ratio of α:β anomer of D-glucose is approximately 1:2.

Figure 3:
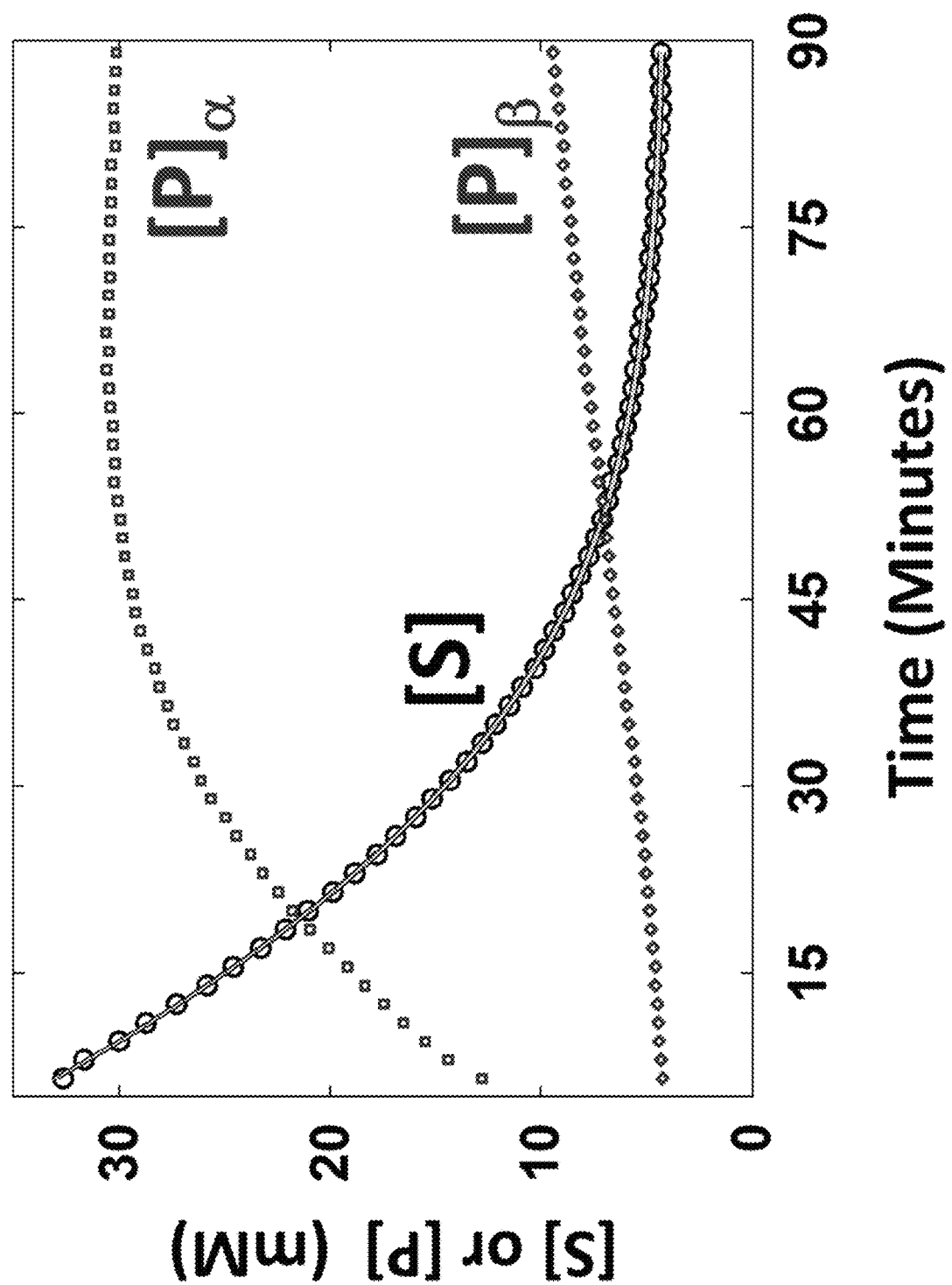
FIG. 3 shows a graph displaying the measurement of concentration of the sucrose substrate and its products as the substrate is broken down over time.

FIG. 3 shows the variation in the concentration of sucrose (substrate, large circles) and glucose (product, small squares) as a function of time due to the hydrolysis process of the enzyme invertase. As expected, the concentration of the sucrose substrate is inversely proportional to the glucose product, specifically the α anomer. Anomerization of α to the β form of the glucose is also observed.

Upon creation of the α-anomer of glucose from sucrose, the interaction with the solvent (in biological systems, water) leads a mutarotation reaction until the equilibrium between α- and β-anomers is reached between α-anomer and β-anomers. The dynamic process that continues until the establishment of thermodynamic equilibrium between both forms is temperature dependent (Franks, Lillford et al. 1989). Mutarotation and formation of anomers is inherent to sugar molecules and most of the sugar molecules exist in multiple anomeric forms (predominantly in α and β-anomers in the case of glucose). Though the co-existence of these multiple anomeric forms is independent of the enzyme action, the amount of the α-anomer of glucose created by the enzyme converts to β-anomer due to interaction with the water molecules in the sample.

D. Effect of Sucralose of the Enzymatic Rate of Conversion of Sucrose

Figure 4:
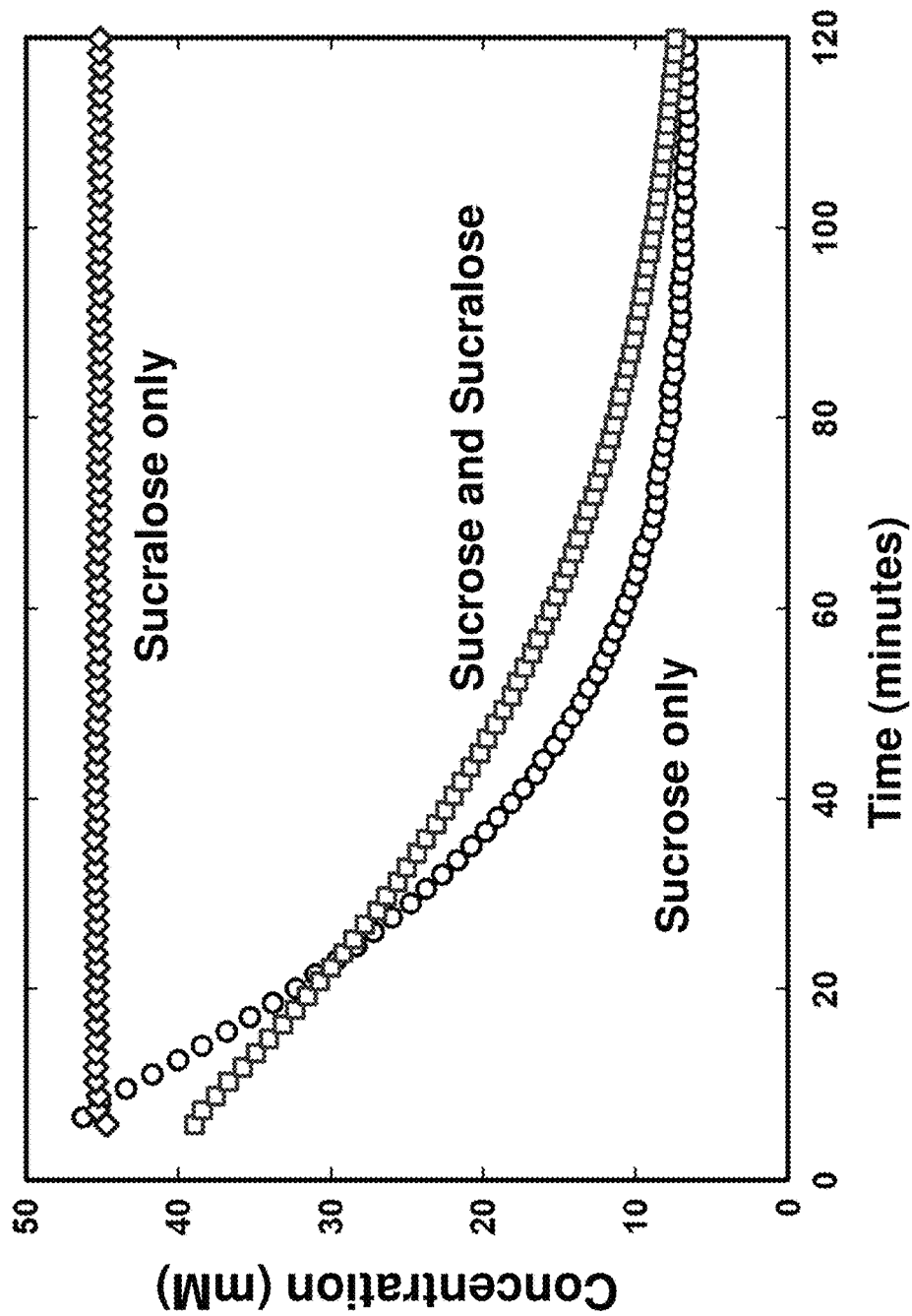
FIG. 4 shows a graph displaying the measurement of concentration of the sucrose substrate—with and without the NAS, sucralose—and the substrate products as the substrate is broken down over time.

To demonstrate the role of sucralose on the enzymatic reaction, FIG. 4 shows the plot of real time measurement of the conversion of the sucrose without sucralose (circle symbols) and in the presence of sucralose (square symbols). Though sucralose concentration remains the same in the experiment (diamond symbols), the presence of sucralose significantly alters the rate at which sucrose is enzymatically converted by invertase. The enzymatic conversion of sucrose to glucose follows the classic Michaelis-Menten enzyme kinetics mechanism (Michaelis and Menten 1913, Briggs and Haldane 1925, Lineweaver and Burk 1934). The enzymatic reaction can be monitored either in terms of the substrate (sucrose) or product (glucose) concentration. The characteristic of the enzyme action, in the absence of any inhibitory process is measured by the Michaelis-Menten parameters defined by the Michaelis-Menten constant ($K_M$) and maximal velocity ($V_{max}$).

By fitting the change in the substrate concentration with time using the Lambert-W function described in equation [5], the Michaelis-Menten constants can be determined directly (Her, Alonzo et al. 2015). For pure enzyme kinetics (no sucralose), the direct method yields a $K_M$ of 50.60 mM±0.91 mM and $V_{max}$ of 2.57±0.03 µM/min.

As shown in FIG. 4, it appears that sucralose slows down the conversion of sucrose to its glucose product. Using the Lambert-W function, the effect of sucralose on the enzymatic conversion of sucrose is performed; this yields a $K_M$ of 68.62 mM±0.99 mM and $V_{max}$ of and 1.87 µM/min±0.01 µM/min.

The physical meaning of $K_M$ (concentration units) represent the state when the half the active sites of the enzyme are occupied by the substrate (sucrose) When the enzyme has a low affinity to the substrate, more number of substrate molecules are required to saturate the active sights leading to a high $K_M$ value. On the other hand, if the enzyme has higher affinity to the substrate then the substrate does not have to occupy a large number of active sites, a small number will suffice leading to a low $K_M$ value. The presence of sucralose (50 mM) increases the $K_M$ value by more than 20%, in other words, the enzymatic activity of the invertase is reduced by 20%. The maximal velocity, $V_{max}$ (in units of rate) represents how fast the enzyme can catalyze the reaction; the number of substrate molecules being catalyzed per unit time. The addition of sucralose simultaneously decreases the maximal velocity by 37%, the rate at which number of sucrose molecules converted to glucose molecules is reduced by the same amount.

As shown in FIG. 4, while sucrose concentration after 120 minutes of enzymatic conversion is the same with or without the presence of sucralose, the sucrose concentration after 60 minutes of enzymatic conversion is different dependent on the presence of sucralose. The starting concentration of the sucrose was 50 mM. After 60 minutes of enzymatic conversion, sucrose in the presence of sucralose has a concentration of about 15 mM. In contrast, after 60 minutes of enzymatic conversion, sucrose without the presence of sucralose has a concentration of about 12 mM. Meanwhile, sucralose itself is not converted in the presence of enzymatic activity that breaks down sucrose.

E. Effect of Sucralose of the Enzymatic Rate of Formation of Glucose

Figure 5:
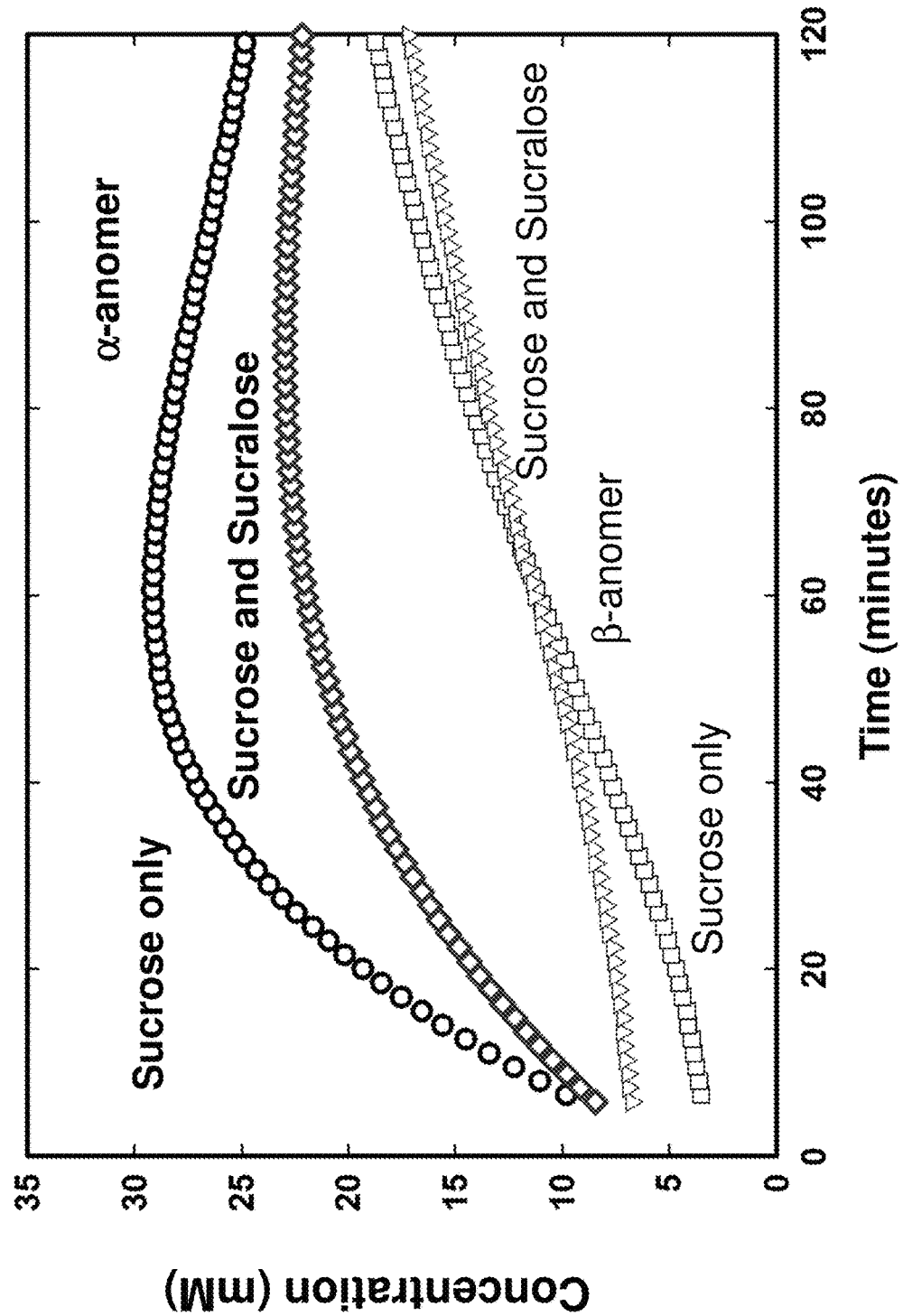
FIG. 5 shows a graph displaying the measurement of concentration of the glucose products—with and without the NAS, sucralose—as the glucose products ($\alpha$-anomer and $\beta$-anomer) are formed from the breakdown of the sucrose substrate over time.

The real time enzyme kinetics approach allows to simultaneously measure the rate of decrease of the substrate (sucrose) and increase of product (glucose) in the same sample. To demonstrate the role of sucralose on the enzymatic reaction, FIG. 5 shows the plot of real time measurement of the formation of glucose in the enzymatic reaction without sucralose (circles and squares) and in the presence of sucralose (diamonds and triangles). Though sucralose concentration remains the same in the experiment (see FIG. 4), contrary to the belief, the presence of sucralose significantly alters the rate at which glucose is enzymatically produced. The production of glucose, vital for energy metabolism, is reduced both in terms of numbers of molecules created as well as the rate at which they are created. The enzyme kinetics parameters in terms of glucose concentration are independently validated using the glucometer data (see FIGS. 10A, 10B and 11). Sucralose reduces the rate at which glucose is formed and it affects the production of both the anomeric forms of glucose. The presence of sucralose alters the production of α-anomers (compare circles and diamonds in FIG. 5) as well as β-anomers (compare squares and triangles, FIG. 5).

As shown in FIG. 5, the concentration of the produced glucose after 120 minutes of sucrose hydrolysis differs between sucrose in the presence of sucralose and sucrose not in the presence of sucralose. After 120 minutes, the α-anomer of glucose measures about 25 mM when sucrose is hydrolyzed without the presence of sucralose. In contrast, after 120 minutes, the α-anomer of glucose measures about 22.5 mM when sucrose is hydrolyzed in the presence of sucralose. After 60 minutes, the α-anomer of glucose measures about 29 mM when sucrose is hydrolyzed without the presence of sucralose. In contrast, after 60 minutes, the α-anomer of glucose measures about 22 mM when sucrose is hydrolyzed in the presence of sucralose.

As shown in FIG. 5, the β-anomer of glucose is also altered in the presence of sucralose. While the concentrations of the β-anomer of glucose formed during the sucrose enzymatic conversion with and without the presence of sucralose is about the same after 60 minutes, the concentrations of the β-anomer of glucose differs after 20 minutes and after 120 minutes. After 60 minutes, the concentrations of β-anomer of glucose formed during the sucrose enzymatic conversion with and without the presence of sucralose is about 10 mM. However, after 20 minutes the concentration of β-anomer of glucose formed during the sucrose enzymatic conversion without the presence of sucralose is about 4 mM. In contrast, after 20 minutes the concentration of β-anomer of glucose formed during the sucrose enzymatic conversion with the presence of sucralose is about 7 mM.

After 120 minutes, the concentration of β-anomer of glucose formed during the sucrose enzymatic conversion without the presence of sucralose is about 19 mM. In contrast, after 120 minutes the concentration of β-anomer of glucose formed during the sucrose enzymatic conversion with the presence of sucralose is about 17 mM. As evidenced by these findings, the relative concentration ratio of the α- and β-anomers of glucose is also altered in the presence of sucralose affecting their natural equilibrium populations.

F. Sucralose Affects the Enzymatic Conversion of Sucrose Even at Low Concentrations.

Figure 6:
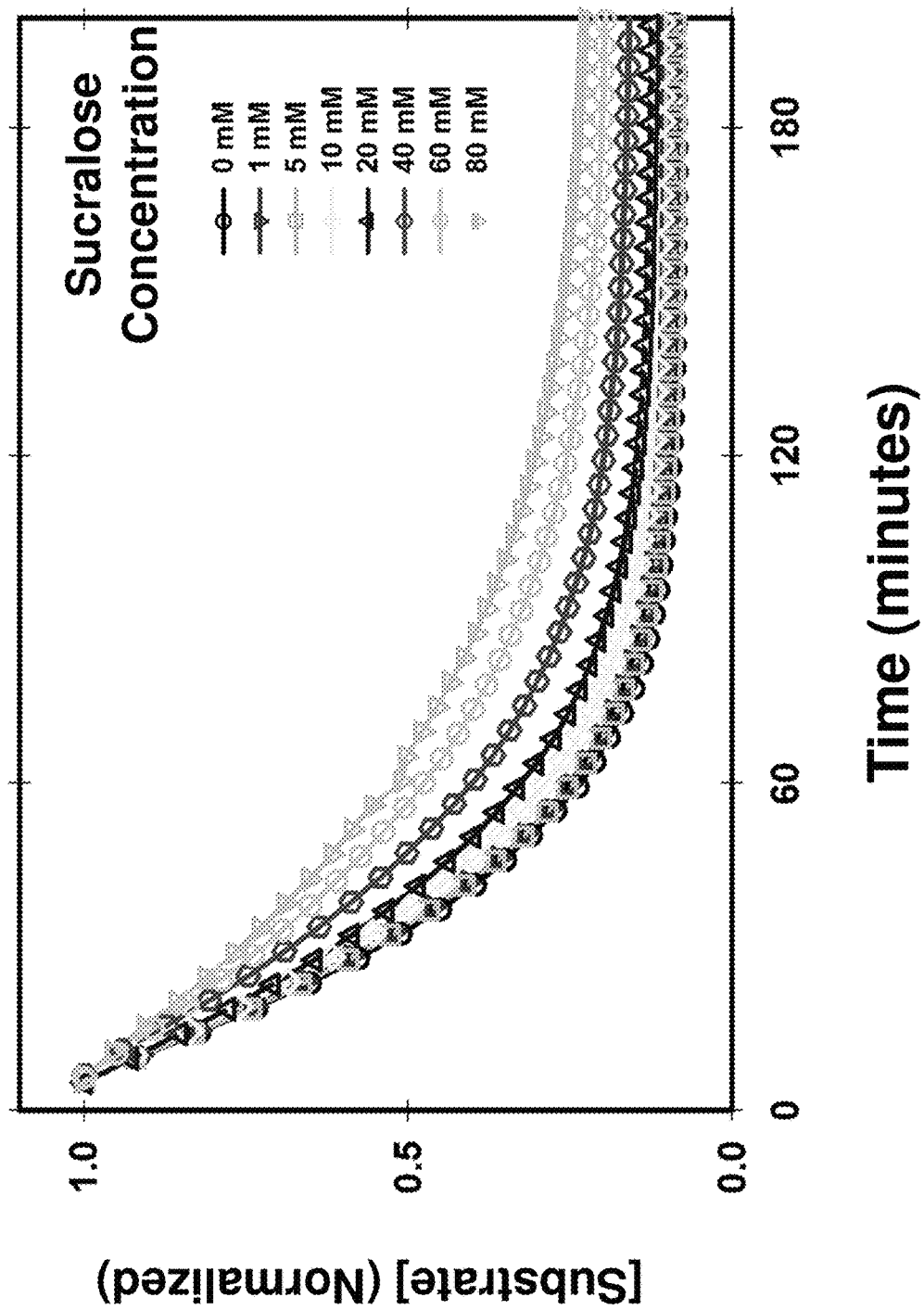
FIG. 6 shows a graph displaying the effects different concentrations of the NAS sucralose has on sucrose substrate breakdown.

The effect of sucralose on the enzymatic kinetics is dynamically linked with the mechanism of catalysis. Observations presented in the earlier charts (FIG. 4) are equimolar concentration (1:1) of sucrose to sucralose (~50 mM) each. The presence of sucralose in the solution affects the catalytic mechanism of the enzyme even at much lower concentrations. FIG. 6 shows the effect of sucralose on the sucrose conversion in the enzymatic reaction at different concentrations of sucralose. The effect of sucralose on the conversion rate of sucrose in the enzymatic reaction is dependent on the concentration of sucralose in the reaction vessel. Sucralose affects the conversion of sucrose even at low concentration. As shown in FIG. 6, the concentrations of sucralose studied were: 0 mM, 1 mM, 5 mM, 10 mM, 20 mM, 40 mM, 60 mM, and 80 mM. Using the progress curve analysis (Equation [5]) the enzyme kinetic parameters (Michalis-Menten parameters) were estimated and the results are shown in Table 1. All the experiments used 40 mM of sucrose and the concentration of sucralose was changed systematically. The higher the concentration of sucralose in the reaction vessel with the sucrose substrate, then the slower the enzymatic conversion rate of the sucrose substrate.

TABLE 1

Effect of Sucralose on the Michalis-Menten using direct NMR method

| Sucralose (mM) | Sucrose:Sucralose | $K_M$ (mM) | $V_{max}$ (µM/min) |
| --- | --- | --- | --- |
| 0 mM | 1:0 | 50.60 ± 0.92 | 2.57 ± 0.03 |
| 1 mM | 40:1 | 56.59 ± 1.30 | 2.71 ± 0.04 |
| 5 mM | 8:1 | 63.27 ± 1.11 | 2.95 ± 0.04 |
| 10 mM | 4:1 | 60.64 ± 0.97 | 2.61 ± 0.03 |
| 20 mM | 2:1 | 64.24 ± 0.90 | 2.49 ± 0.02 |
| 40 mM | 1:1 | 68.58 ± 1.15 | 2.25 ± 0.02 |
| 60 mM | 1:1.5 | 68.62 ± 0.99 | 1.87 ± 0.02 |
| 80 mM | 1:2 | 73.93 ± 1.19 | 1.72 ± 0.02 |

G. Sucralose Affects the Enzymatic Formation Both α- and β-Anomers of Glucose Resulting from Sucrose Enzymatic Conversion in the Presence of Different Sucralose Concentrations.

Figure 7:
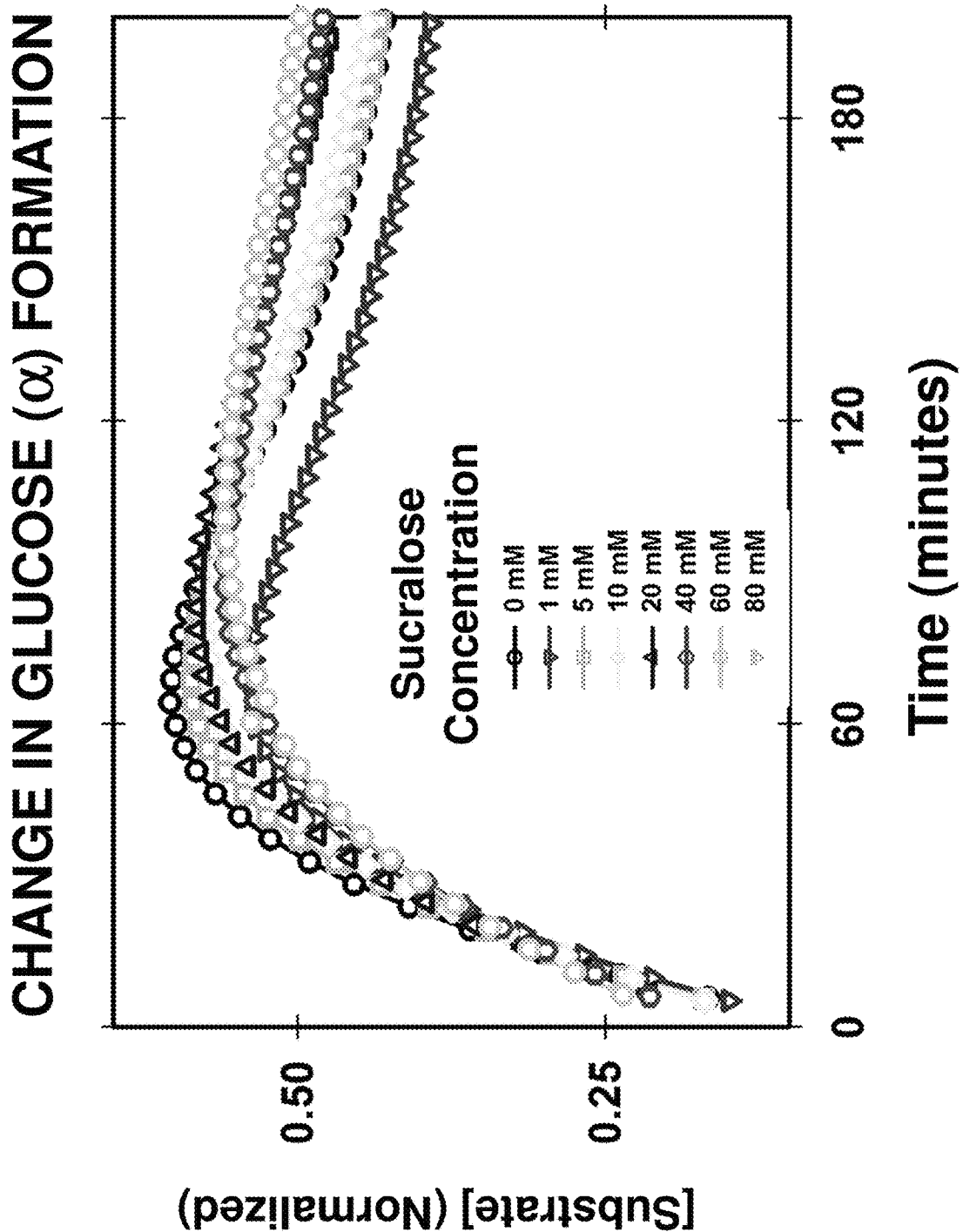
FIG. 7 shows a graph displaying the effects different concentrations of the NAS sucralose has on a glucose product ($\alpha$-anomer) production in light of the sucrose substrate breakdown.

Concentration effects of sucralose are significant on the enzymatic creation of glucose molecules as the enzymatic kinetics dynamically linked catalytic process of the enzyme. Observations presented in the earlier charts (FIG. 5) are equimolar concentration (1:1) of sucrose to sucralose (50 mM) each. FIG. 7 shows the effect of sucralose on the formation of α-anomer of glucose resulting from the sucrose conversion in the enzymatic reaction at different concentrations of sucralose. Sucralose affects the formation of the α-anomer of glucose even at low concentration.

As shown in FIG. 7, the concentration of sucralose studied were: 0 mM, 1 mM, 5 mM, 10 mM, 20 mM, 40 mM, 60 mM, and 80 mM. The higher the concentration of sucralose in the reaction vessel with the sucrose substrate, the Michalis-Menten constant ($K_M$) of the reaction systematically increases (Table 1). As noted before (FIG. 4 and FIG. 5), increasing the $K_M$ means that the efficiency of the enzyme is lowered. As shown in FIG. 7, the concentrations of sucralose studied were: 0 mM, 1 mM, 5 mM, 10 mM, 20 mM, 40 mM, 60 mM, and 80 mM. At 1:2 ratio of the sucrose:sucralose concentrations, the $K_M$ value increase almost by 50% (or enzyme catalytic activity inhibited by 50%) by the sucralose molecule (Table 1). Similarly, the maximal velocity ($V_{max}$) decreases approximately by 33%, in the above mentioned ratio. Taken together (enzyme affinity defined by $K_M$ and rate of conversion $V_{max}$), the overall efficiency of the enzyme kinetics is lowered significantly both in terms of rate production and quantity of glucose molecules produced.

Figure 8:
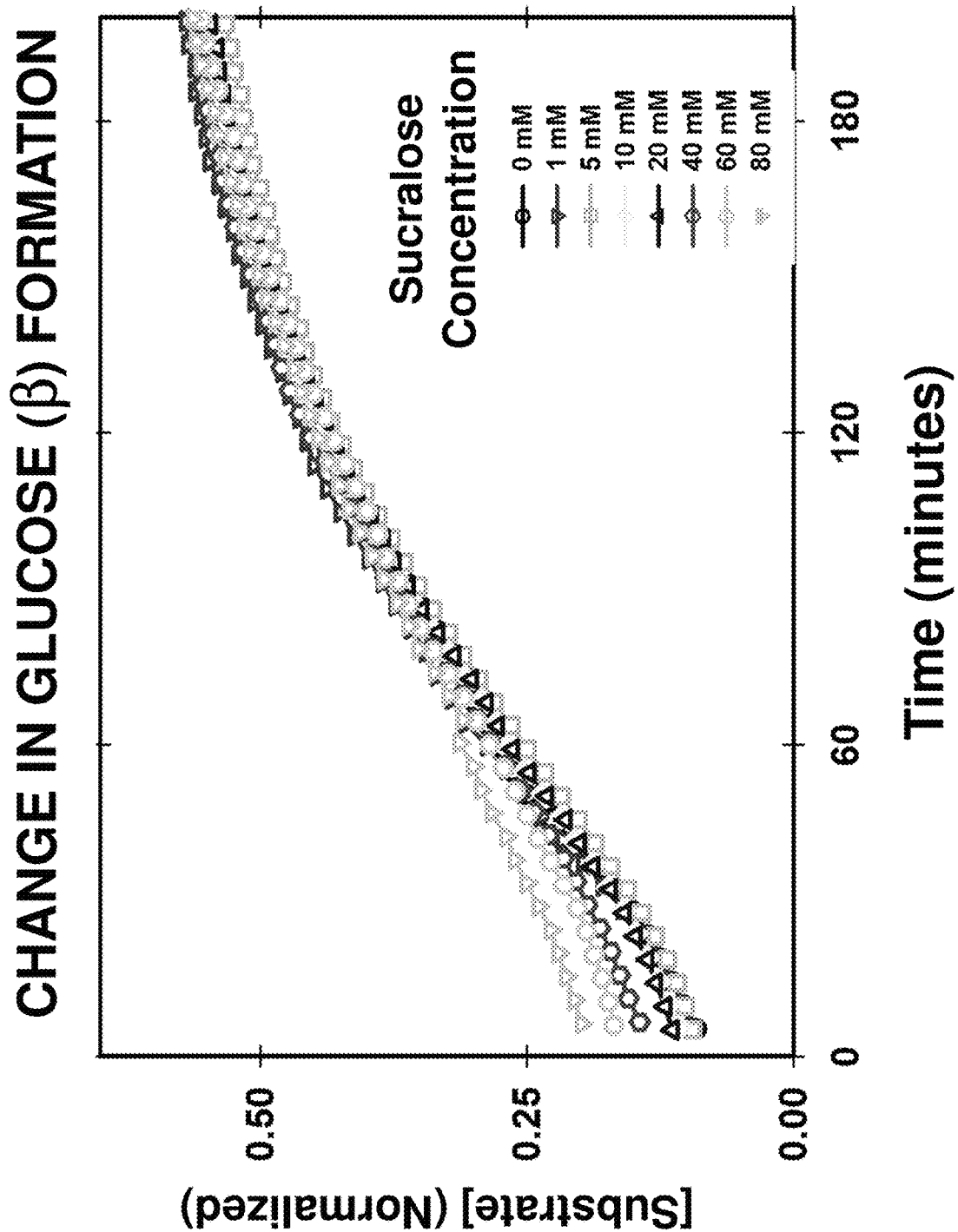
FIG. 8 shows a graph displaying the effects different concentrations of the NAS sucralose has on a glucose product ($\beta$-anomer) production in light of the sucrose substrate breakdown.

Enzyme invertase converts the sucrose to glucose in its α-anomeric form. The interaction of α-anomer with water starts converting to the β-anomer (FIG. 5). FIG. 8 shows the effect of sucralose on the formation of β-anomer of glucose resulting from the sucrose conversion in the enzymatic reaction at different concentrations of sucralose. As shown in FIG. 8, the concentrations of sucralose studied were: 0 mM, 1 mM, 5 mM, 10 mM, 20 mM, 40 mM, 60 mM, and 80 mM. Sucralose affects the formation of the β-anomer of glucose even at low concentration. The higher the concentration of sucralose in the reaction vessel with the sucrose substrate, due to low production of α-anomer, the rate and quantity of β-anomer produced is also significantly lowered. Though the conversion of α-anomer to the β-anomer is not affected by the enzyme directly, sucralose alters the concentration of glucose produced in lowering the efficiency of the enzyme kinetics, thus altering the β-anomeric concentration as well. With increasing sucralose concentration the reaction progress curve becomes more linear (in time) and losing the characteristic features and advantages of enzyme mediated catalytic reaction process.

H. Direct Analysis of the Enzyme Kinetics Using Lambert-W Function

Figure 9:
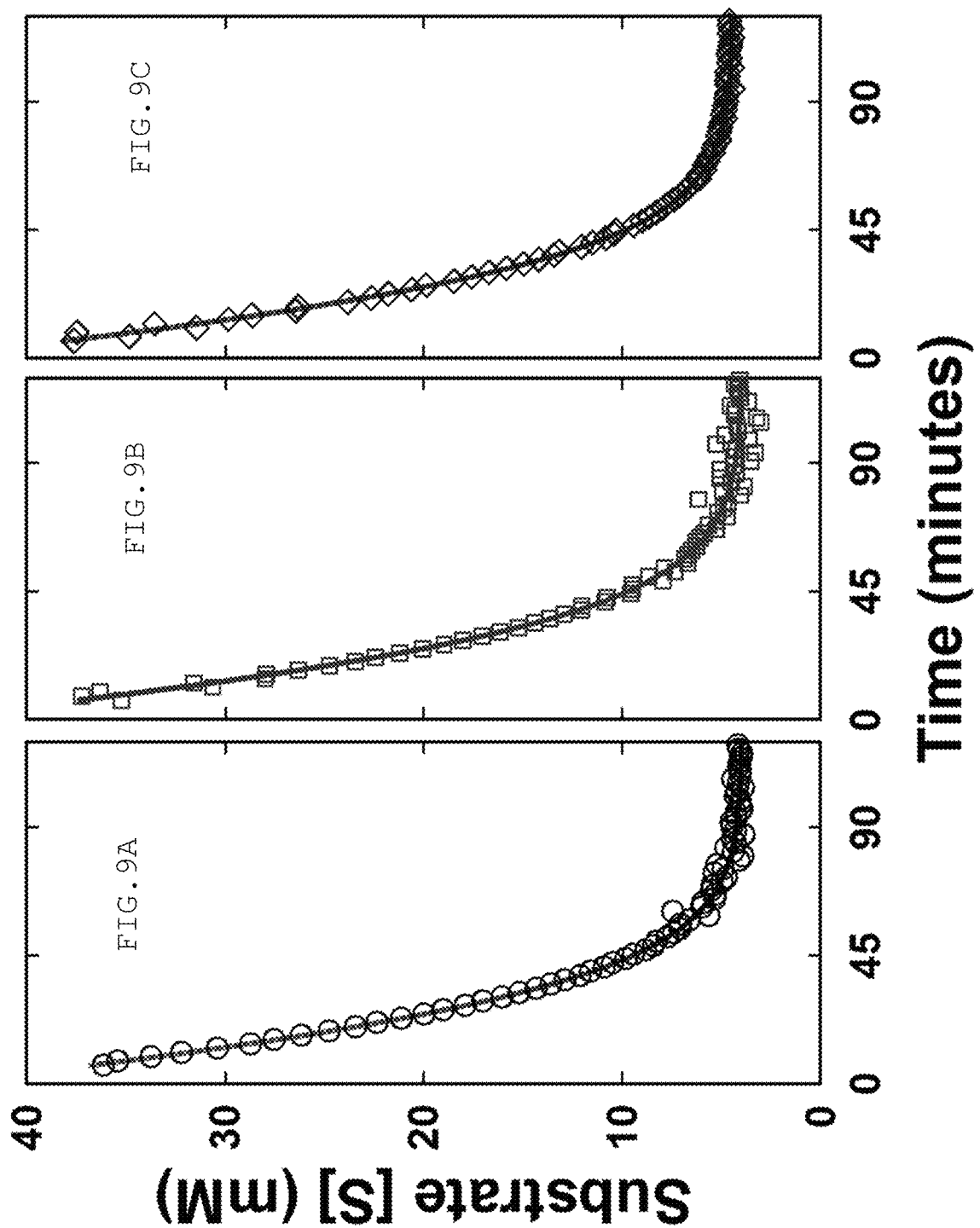
FIGS. 9A-9C show graphs displaying the analysis of the real time sucrose substrate breakdown data using the Lambert-W function. Each one of FIGS. 9A, 9B and 9C independently show the real time sucrose substrate breakdown data using the Lambert-W function. Together, FIGS. 9A-9C demonstrate the reproducibility of the experimental measurement and the consistency of the data.

In these findings, the time dependent reaction mechanism is analyzed using direct progress curve analysis (Equation [5]) (Her, Alonzo et al. 2015). The sensitivity and consistency of analysis is demonstrated; FIGS. 9A-9C_show the progression of the kinetics for the substrate concentration as a function of time for three independent trials. For each independent trial, the progress curve was analyzed by fitting the data points to equation [5] and Table 2 shows the results of the analysis. The average coefficient variation (coefficient variation (CV) in %) of $K_M$ measured from the three trials is 9% and that of the $V_{max}$ is 7%. For each trial, the starting concentration of sucrose was 42 mM and no sucralose was added. Progress curves were analyzed using R statistical environment (https://www.r-project.org/, version 3.2.1).

TABLE 2

Estimated Michaelis-Menten parameters using qNMR data

| Michaelis-Menten Parameters | Trial 1 | Trial 2 | Trial 3 | Average |
| --- | --- | --- | --- | --- |
| $K_M$ (mM) | 34.69 ± 3.96 | 43.59 ± 11.90 | 37.44 ± 7.79 | 38.57 ± 3.72 |
| $V_{max}$ (µM/min) | 2.34 ± 0.18 | 2.77 ± 0.54 | 2.51 ± 0.36 | 2.54 ± 0.18 |
| $[S]_o$ (mM) | 41.27 ± 0.39 | 42.91 ± 0.88 | 42.05 ± 0.69 | 42.08 ± 0.67 |

Figure 10:
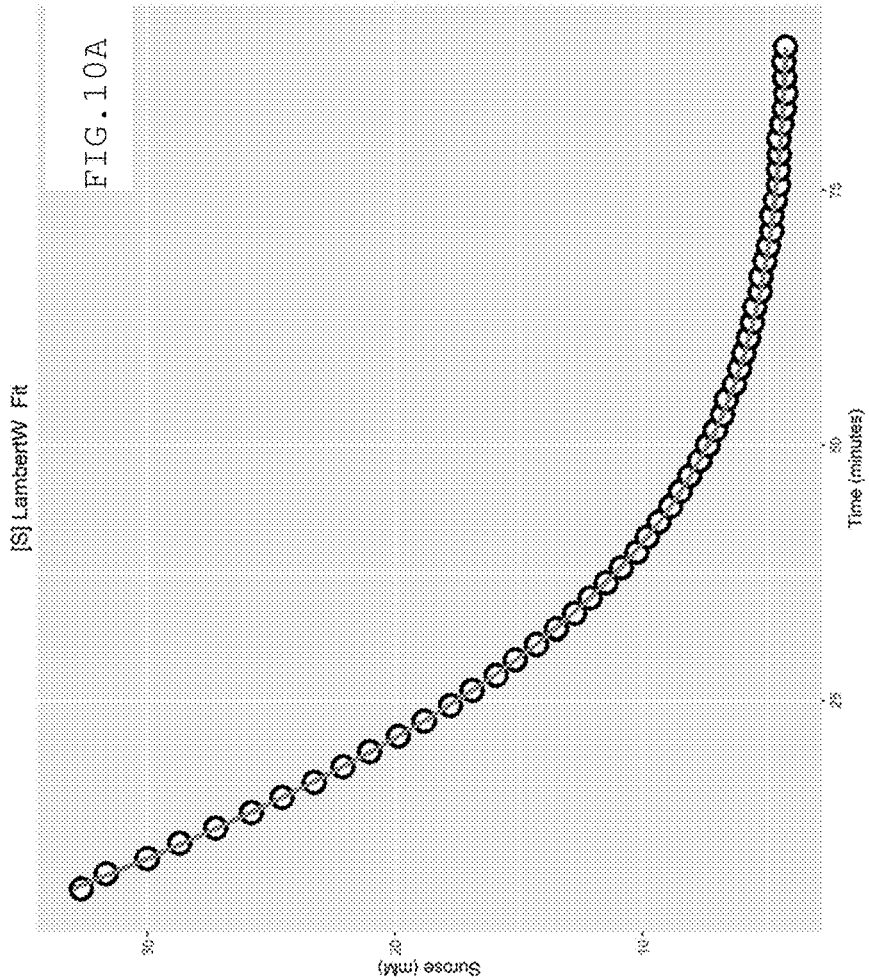
FIG. 10A shows an output chart generated using the code written to fit the experimental data.
FIG. 10B shows a table including the statistical analysis data of the fit of the output chart.

The spectrometer software is used to find the integration under each peak of the sucrose (5.41 ppm) and TSP (0.0 ppm). The concentration of the sucrose peak is calculated with reference to the known concentration of TSP. If multiple experiments are performed, averages and standard deviations of the integrations of the trials at each temperature is calculated. A two-column excel or text (tab limited format) with X=Time and Y=[S] is produced as the input to the R-program. The written code utilizes the following external libraries: spatstat and gsl (to implement functions such as LambertW function), xtable (for table manipulations) and ggplot2 (to make plots (optional)). An example of the output produced is shown in FIGS. 10A-10B. The R-code reads the input file and creates a data fit, statistics and plot with the experimental and fitted values. Typically the procedure works with a minimum of 15 time points sampled uniformly over the experimental time period chosen and it utilizes a non-linear least square fitting procedure. In addition to generating a plot (FIG. 10A), the code generates a file in picture format (.png) and a tab-limited text file that can be imported into other plotting routines. The statistical parameters of the fit (FIG. 10B) are also available in a tabular form for reporting purposes, which includes the fitted values (Coef.), standard error of the fit, t-statistics and p-value for each of the parameters. If the signal has not decayed to zero, an additional parameter (FIG. 10B) can be used as an offset. The direct progress curve analysis in the presence of sucralose (data shown in FIG. 6) reveals a similar coefficient of variation (3%-5%) for the respective measurement of each of $K_M$ and $V_{max}$.

Direct progress curve analysis has unique advantages in comparison with traditional analysis of enzyme kinetics. Specifically, four advantages are: (1) Direct progress curve approach can follow the reduction of the substrate (sucrose) and generation of the product (glucose) due to enzymatic reaction dynamics in real time. (2) The concentration of the reactants and products are determined with one known concentration, the starting concentration of substrate (sucrose). (3) The analysis is done by following the reaction of the substrate (sucrose) rather than that of the product (glucose). This is particularly important in the case of conversion of sucrose to glucose as the glucose α-anomer starts converting to its β-anomer. (4) Though the analysis can also be performed on measuring the product progress, it would be necessary to include the peak intensities at both the α and β anomers to account for the total glucose.

I. Validation of NMR Results Using Glucometer Measurements

Figure 11:
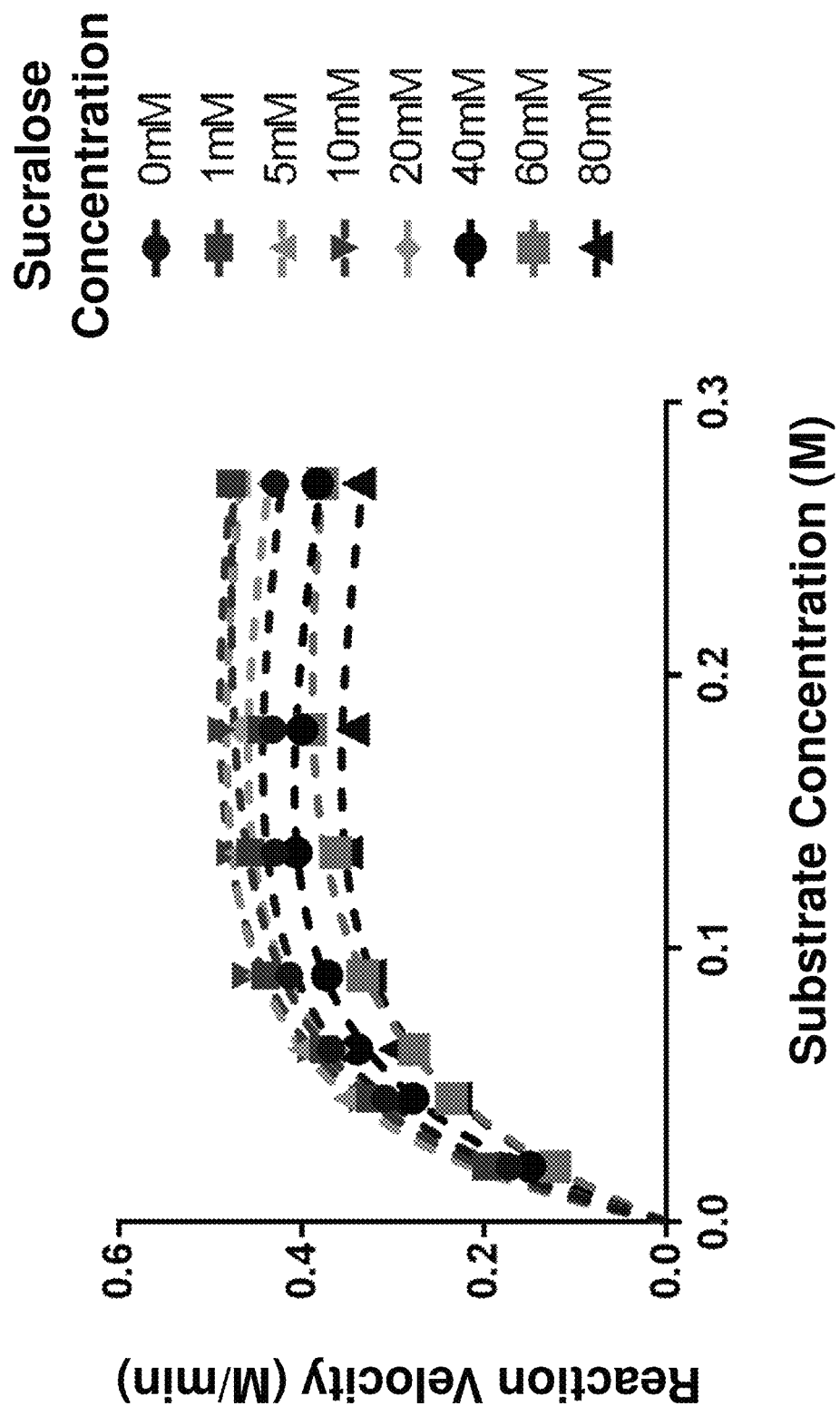
FIG. 11 shows a graph displaying glucometer data representing Michaelis-Menten kinetics (substrate concentration vs. reaction velocity) as a function of increasing concentration of sucralose.

NMR based direct progress curve analysis is capable of measuring the enzyme kinetics of invertase and the effect of sucralose on the quantitative Michaelis-Menten parameters. Michaelis-Menten mechanism of enzyme kinetics was first described more than 100 years ago (Michaelis and Menten 1913) for the enzyme invertase. The enzyme kinetics measurements are routinely used in both academics and in industry. Therefore we validate the NMR based real time progress curve analysis as well as the effect of sucralose on the enzyme kinetics, using the Michaelis-Menten method. In order to validate the NMR based real time measurements developed in this study, glucometer based measurements were performed. FIG. 11 shows the plot of Michaelis-Menten kinetics (substrate concentration vs. reaction velocity) as a function of increasing concentration of sucralose. Glucometer based approach is based on the electrochemical mechanism of the interaction between glucose oxidase (present in the test strip) and the glucose in the sample (Heller and Feldman 2008). However, the glucometer approach can measure the glucose level, one sample at a time (per test strip) and does real time changes cannot be followed. FIG. 11 data was recorded by the OneTouch Vita system from LifeScan, a system that is available worldwide and has a double electrode system to control the accuracy of the results (Young, Ellison et al. 2008). When inserted into the solution, the sensors automatically absorb a sample of 0.6 μL within a second and the meter produces the result within 5 seconds. Up to 500 results can be stored in the meter and could be transferred to a computer. Within the experiments, the standard deviations were within 5%.

As shown in FIG. 11, the concentrations of sucralose studied were: 0 mM, 1 mM, 5 mM, 10 mM, 20 mM, 40 mM, 60 mM, and 80 mM. As shown in FIG. 11, standard Michaelis-Menten analysis of the experimental data demonstrates the effect of increasing concentrations of sucralose alters the overall enzyme kinetics in a systematic manner, leading to a lowered enzyme activity with increasing sucralose concentration. The lowered enzyme activity is shown by the flattened reaction velocity plot lines as a result of increased sucralose concentration. At a substrate concentration of 0.1 M, the reaction velocity of the sucrose was over 0.4 M/min when the sucrose was reacted in the presence of sucralose having a concentration of 20 mM or lower. At a substrate concentration of about 0.27 M, the reaction velocity of the sucrose was over 0.4 M/min when the sucrose was reacted in the presence of sucralose having a concentration of 20 mM or lower. These results support the evidence presented using the progress curve analysis and confirm that sucralose does affect the enzymatic activity.

J. Role of Sucralose on Enzyme Activity

Figure 12:
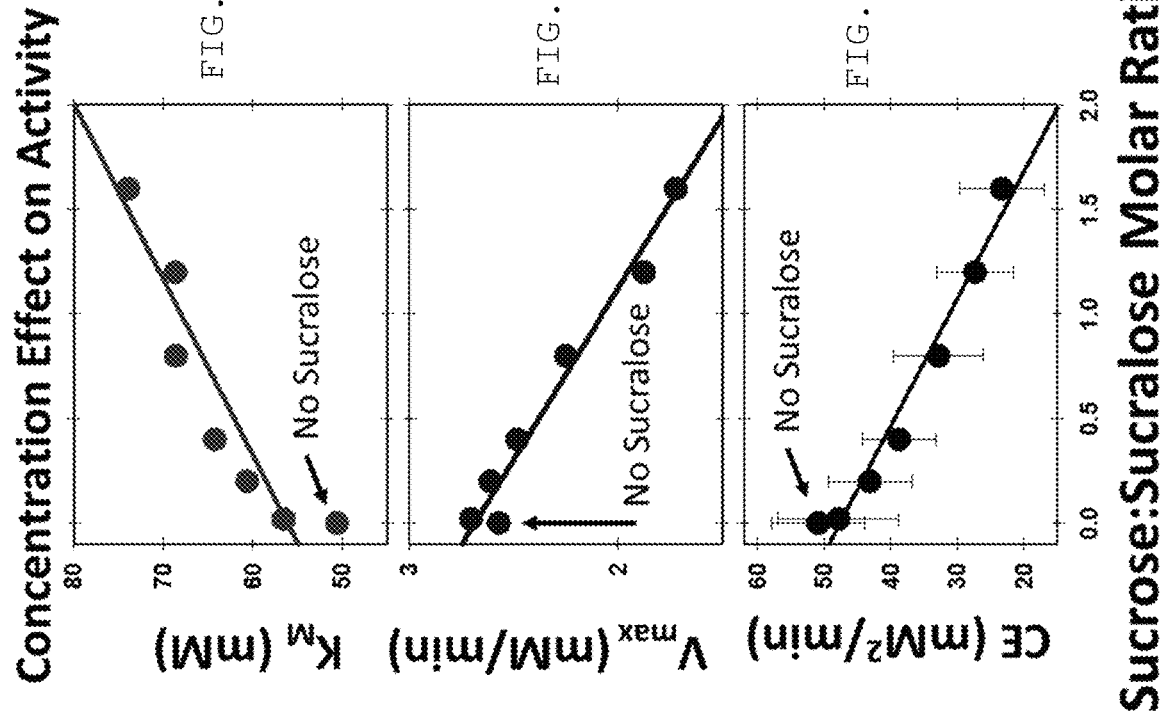
FIGS. 12A-12C show charts summarizing the effects of sucralose on biological enzymatic activity.

The real time NMR based progress curve analysis demonstrates the deleterious effects of sucralose in the overall enzyme kinetics. These aspects are also independently validated in the traditional Michaelis-Menten enzyme kinetics using a glucometer. The summary of the effect on the enzymatic activity is shown in FIGS. 12A-12C. Increasing the sucralose concentration increases the $K_M$ values (FIG. 12A) and decreases the $V_{max}$ (FIG. 12B) in an effectively linear manner. When no sucralose is present in the solution the enzyme kinetics measurement is distinctly different (see pointers in FIGS. 12A-12C). The regression line shown in FIGS. 12A and 12B were calculated using SigmaPlot (http://www.sigmaplot.com, version 12.5). From the regression analysis, the $K_M$ value (FIG. 12(*a*)) increases by 9.78±1.44 mM per unit increase (mM) increase of sucralose while the $V_{max}$ value (FIG. 12B) decreases by 6.54±0.03 μM/min per unit increase of sucralose.

Using the definition by Koshland (Koshland Jr., 2002), catalytic efficiency of the enzyme activity is also shown in FIG. 12C. Catalytic efficiency provides insight into enzymatic mechanisms and the functional effects on sucralose concentrations on activity. The roles of many enzymes in a biological system that are related by the chemical kinetics and equilibrium processes are extremely important for the overall function many important biochemical reactions. In the absence of catalytic process the rate at which the products are forms is slow. Without invertase it would take many days for the sucrose to convert to glucose purely by acid hydrolysis. Enzymes lower the activation barrier of the reaction so that the reaction rate is increased, consequently the more product is produced. Biological functions are made of cascade of multiple reactions where the product from one specific reaction (glucose) might serve as a reactant to another reaction (glucose transport). With multiple enzymes involved in the overall function, the efficiency of each enzyme defined by its 'catalytic efficiency' leading to an optimized and efficient chemical reaction within a biological system.

As shown in FIG. 12C, the overall efficiency of the enzyme function is significantly decreased, more or less in a linear fashion with increasing concentration of sucralose. The regression line shown in FIG. 12C estimates that the catalytic efficiency of the enzyme decreases by 152.1 mM$^2$/min±1.31 mM$^2$/min, per unit increase of sucralose (in mM)

Figure 13:
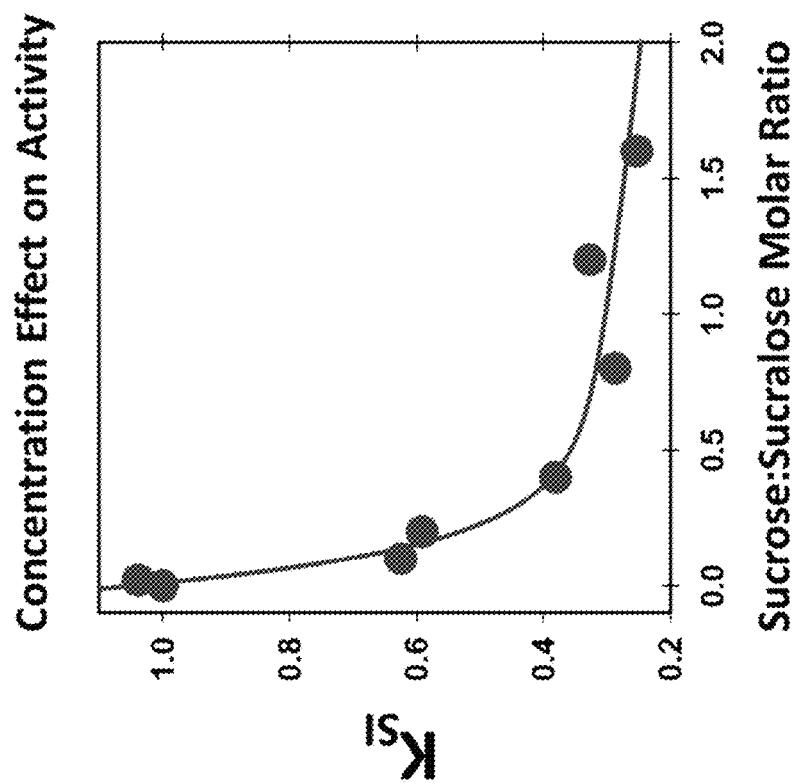
FIG. 13 shows a graph plotting the inhibition constant ($K_{SI}$) as a function of the molar ratio of sucrose to sucralose.

As shown in FIG. 11, the glucometer data were collected in a traditional approach to determine the relation between the substrate concentration ([S]) and reaction velocity as a function of sucralose concentration. A substrate inhibition model tends to fit the data better and outcome of the analysis is shown in FIG. 13. As shown FIG. 13, the plot of the inhibition constant as a function of the molar ratio of sucrose to sucralose shows an exponential behavior. Even smaller amount of sucralose tend to inhibit the enzyme activity.

As shown in FIG. 13, the continuous inhibition model curve suggests that the substrate is inhibited by more than 50% at a molar of ratio of sucrose to sucralose at 1:0.25 and the trend continues to reach a plateau at 1:1 ratio.

K. Functional Implications

The first step in the metabolism of digestible sucrose is its conversion to the simpler, soluble monosaccharide forms (glucose and fructose) that can be transported across the intestinal wall and delivered to the tissues. This process is done by enzyme activated hydrolysis and the resultant glucose and fructose are transported into the intestinal enterocytes via the actions of various carbohydrate transporters. In the cascade of reactions that follow the rate of glucose (or fructose) transport depends primary on the production rate of the glucose (or fructose) by the enzyme kinetics.

Glucose metabolism and insulin production is highly important for the overall glucose metabolism. Presence of glucose in the blood as a results of food intake, triggers the release of insulin. Insulin is important is regulating the many other pathways that allows the distribution of glucose to muscle and fat cells via glucose transporters. The level of insulin, which is triggered by the presence of glucose in the blood also play an important role in determining whether the glucose could be stored as glycogen, as an energy storage in the cell. When the cells need additional energy (glucose) the hormone glucagon is released to signal the breakdown of glycogen to glucose in the blood. The complex dynamics between the glucose and other elements in the cell are defines the process of homeostasis that maintains a relatively constant blood sugar level (Bogan 2012). Rate of metabolic flow (also known as flux) through the homeostatic mechanisms pathway is high, but concentration of substrate/intermediates/products remains constant. If this steady state is disrupted, by external change rate of glucose formation, the pathway will change and regulatory mechanisms will be triggered thus the organism will try to arrive at a new steady state to achieve homeostasis. Therefore, from a simple coupled reaction point of view, the rate of glucose production is expected to affect the energy homeostasis and the rest of the downstream pathways related glucose metabolism.

We have invented a method for obtaining enzyme-kinetic parameters from time-course data of reactants generated using NMR spectroscopy or a glucometer to study the effects of sucralose on sucrose substrate breakdown. The method requires fewer experimental runs, less sample amounts than traditional initial-rate based studies, yielding more information per experiment. Additionally, this approach allows real-time simultaneous quantification of both the substrate and product(s) present in the assay system, which demonstrates the superiority of qNMR over traditional enzyme assays using spectrophotometric methods. The methodology presented may be applied to the elucidation of kinetic parameters for invertase catalyzed conversion of sucrose to glucose and fructose and may be established for other enzyme kinetics experiments A number of embodiments of the invention have been described. Nevertheless, it will be understood that various modifications may be made without departing from the spirit and scope of the invention. Accordingly, other embodiments are within the scope of the present invention.

We claim:

1. A method of measuring the effect of an artificial sweetener on enzyme-catalyzed hydrolysis of a sugar in real time comprising:
    (a) establishing a first sugar enzymatic conversion rate by measuring the rate said sugar breaks down to reaction products in the presence of an enzyme;
    (b) determining a second sugar enzymatic conversion rate by measuring the rate said sugar breaks down to reaction products in the presence of said enzyme and said artificial sweetener; and
    (c) comparing said first sugar enzymatic conversion rate and said second sugar enzymatic conversion rate in real time and fitting the substrate concentration with time using equation [5]

$$[S] = K_M W\left\{\frac{[S]_o}{K_M} \exp\left(\frac{[S]_o - V_{max} t}{K_M}\right)\right\} \quad [5]$$

wherein ([S]) is the substrate concentration at any time and ([S]$_0$) is its initial concentration, is the maximal rate of enzymatic turnover, $K_M$ represents Michaelis-Menten half-saturation constant, t is time, W is any complex number, so as to determine the Michealis-Menton constants which reflects the effect of artificial sweetener on enzyme-catalyzed hydrolysis of sugar in real time,
    wherein W corresponds to Lambert-W function which is integrated in the Michealis-Menten Kinetics equation as follows:
    the Michaelis-Menten equation in differential form Equation [1]:

$$V = \frac{d[P]}{dt} = -\frac{d[S]}{dt} = \frac{V_{max}[S]}{K_M + [S]} \quad [1]$$

equation [1] is integrated to yield an integral form of the Michaelis-Menten equation [2]:

$$K_M \ln\left(\frac{[S]_0}{[S]}\right) + [S]_0 - [S] = V_{max} t \quad [2]$$

Lambert-W function is an exponential function in which the exponential function and natural logarithmic function ln(x) are exponentially related as such, W(x) is defined as the inverse of the function satisfying $ye^y = x$ and its solution expressed by the Lambert-W(x) function as y=W(x);
    substituting y=[S]/$K_M$ in Equation [2], Equation [3] is obtained;

$$ye^y = x(t) = \exp\left(\frac{[S]_0 - V_{max} t}{K_M} + \ln\left(\frac{[S]_0}{K_M}\right)\right) \quad [3]$$
$$= \frac{[S]_0}{K_M} \exp\left(\frac{[S]_0 - V_{max} t}{K_M}\right)$$

left hand side of Equation [3] is analogous to Lambert-W function, using the definition of Lambert-W function y=W(x)), an expression for y is obtained as that expressed in Equation [4]:

$$y = W\left\{\frac{[S]_0}{K_M}\exp([S]_0 - V_{max}t/K_M)\right\} \quad [4]$$

further substituting $y=[S]/K_M$ back in Equation [4], Equation [5] is obtained.

2. A method according to claim 1, wherein said first sugar enzymatic conversion rate is established by nuclear magnetic resonance.

3. A method according to claim 1, wherein said second sugar enzymatic conversion rate is determined by nuclear magnetic resonance.

4. A method according to claim 1, wherein said first sugar enzymatic conversion rate and said second sugar enzymatic conversion rate are determined by nuclear magnetic resonance.

5. A method according to claim 1, wherein said first sugar enzymatic conversion rate is established by a glucometer.

6. A method according to claim 1, wherein said second sugar enzymatic conversion rate is determined by a glucometer.

7. A method according to claim 1, wherein said first sugar enzymatic conversion rate and said second sugar enzymatic conversion rate are determined by a glucometer.

8. A method according to claim 1, wherein said comparing step results in a numerical value associated with said artificial sweetener.

9. A method according to claim 1, wherein said enzyme is invertase.

* * * * *

UNITED STATES PATENT AND TRADEMARK OFFICE
CERTIFICATE OF CORRECTION

PATENT NO. : 10,612,071 B2
APPLICATION NO. : 15/079647
DATED : April 7, 2020
INVENTOR(S) : Krishnan et al.

Page 1 of 1

It is certified that error appears in the above-identified patent and that said Letters Patent is hereby corrected as shown below:

In the Claims

In Column 14, Line 23, in Claim 1, after "concentration,", insert --$V_{max}$--.

In Column 14, Line 66, in Claim 1, delete "y=W(x))," and insert --(y=W(x)),-- therefor.

Signed and Sealed this
Sixteenth Day of June, 2020

Andrei Iancu
*Director of the United States Patent and Trademark Office*